US008005349B2

(12) United States Patent
Deflorian et al.

(10) Patent No.: US 8,005,349 B2
(45) Date of Patent: Aug. 23, 2011

(54) ELECTRIC EVAPORATOR DEVICE OF VOLATILE SUBSTANCES WITH ADJUSTABLE EVAPORATION INTENSITY

(75) Inventors: Stefano Deflorian, Trento (IT); Walter Sordo, Trento (IT); Franco Zobele, Trento (IT)

(73) Assignee: Zobele Holding S.p.A. (IT)

( * ) Notice: Subject to any disclaimer, the term of this patent is extended or adjusted under 35 U.S.C. 154(b) by 828 days.

(21) Appl. No.: 11/875,502

(22) Filed: Oct. 19, 2007

(65) Prior Publication Data
US 2008/0095522 A1   Apr. 24, 2008

(51) Int. Cl.
*A01G 13/06* (2006.01)
(52) U.S. Cl. ........................................ 392/387; 392/386
(58) Field of Classification Search .......... 392/386–406; 134/12; 165/200–303; 208/308; 239/1–13; 431/13; 432/13
See application file for complete search history.

(56) References Cited

U.S. PATENT DOCUMENTS

| 4,647,428 A | * | 3/1987 | Gyulay | 422/4 |
| 4,675,504 A | * | 6/1987 | Suhajda | 392/390 |
| 5,616,265 A | * | 4/1997 | Altman | 219/497 |
| 7,149,417 B2 | * | 12/2006 | Joshi et al. | 392/390 |
| 2008/0095522 A1 | * | 4/2008 | Deflorian et al. | 392/387 |

* cited by examiner

*Primary Examiner* — Daniel Robinson
(74) *Attorney, Agent, or Firm* — Ostrolenk Faber LLP

(57) ABSTRACT

The present invention relates to an electric evaporator device of volatile substances with adjustable evaporation intensity. A heating plate (4) defines a first chamber (6) separated from a second chamber (8), wherein a heat generator (5) is located inside the first chamber (6). A regulation opening (13), located in the first chamber (6), allows the exit of a heated air flow from the first chamber to regulate the temperature both in the first chamber (6) and the heating plate (4), enabling thus the regulation of the evaporation rate.

4 Claims, 9 Drawing Sheets

ELECTRIC EVAPORATOR DEVICE OF VOLATILE SUBSTANCES WITH ADJUSTABLE EVAPORATION INTENSITY

CROSS REFERENCE TO RELATED APPLICATION

The present invention is based on and claims priority to Provisional Application No. 60/862,339 which was filed Oct. 20, 2006, the contents of which are specifically incorporated by reference herein.

FIELD OF THE DISCLOSURE

The present invention relates to an electric evaporator device of volatile substances with adjustable evaporation intensity, of the type of those which are connected to the electricity mains to emit a fragrance or an insecticide by heating process, and in particular to an evaporator for liquid formulations.

The invention can be usefully applied in the field of electric evaporators for diffusing perfumes or insecticides into the atmosphere, preferably in the home range.

An object of the invention is to enable the emanation flow of active substance emitted to be continuously regulated between a minimum and a maximum level, and avoid the escape of liquid outside the device when an accidental increase of the power supply occurs, thus protecting the device.

DESCRIPTION OF RELATED ART

Electric vaporizer devices of volatile substances are known which evaporate perfumes or insecticides into the surrounding atmosphere by adapting to domestic electric power sockets, comprising a container of the volatile substance, a resistive heating element and means for activation by manual or automatic operation with an operatively associated electronic circuit.

There is a particular type of devices having at least a closed container of the active or volatile substance, usually liquid substance, that comprises a flat wall or membrane apt to be crossed through by the emanated vapours, but not by the liquid, of the volatile substance.

When the container is emptied or when the user wants to change the liquid the container has to be replaced with another new one.

In the field of electric home evaporators used with liquid formulations, evaporators are already known wherein the intensity of evaporation of the active substance may be adjusted by modifying the relative position of the heating means, which is normally an electric resistance, with respect to that of the membrane of the container containing the liquid solution of active substance. Furthermore, evaporators are already known wherein said intensity is manually adjusted by modifying the area of an opening located between the container and the surrounding atmosphere.

The main drawback of the above-described devices is that the consumption rate of the volatile substance is always the same, regardless of the position of the regulation means. In the other hand said evaporation adjustment system allows only two-position adjustment, i.e. either a minimum flow or a maximum flow, and therefore it is not possible to adjust with continuity and precision the evaporation flow between a minimum level and a maximum level. Finally, said devices have a security problem in case of an accidental increase of the power supply occurs, producing the breakage of the membrane, due to the excessive temperature of the heating means, and thus the escape of the liquid contained in the container.

SUMMARY

The electric evaporator device of volatile substances with adjustable evaporation intensity which constitutes the object of this invention allows a continuous regulation of the emanation intensity rate, by the regulation of the consumption rate of the liquid formulation, also with the objective to arrange a secure device avoiding escapes of liquid due to any accidental circumstances respecting the supply.

The object of the present invention is therefore to provide an electric evaporator for volatile substances, i.e. insecticides or fragancies, of the type for use with liquid formulations, in which it is possible to obtain an optimum and continuous adjustment in the flow of evaporated active substance between a minimum level and a maximum level, without the need for use of complex mechanisms and also avoiding any displacement of the electrical connections of the heating device during the evaporator-flow adjustment operations.

The main aim of the present invention is to realise a dispenser which enables an intensity of the vapours dispensed into the air to be regulated, thus increasing the temperature of resistance elements which results in an increase in vaporization rate and therefore in a greater vaporization of the fragrances into the atmosphere.

There is also aim of the present invention to have a very low energy transfer towards the membrane, as security means, in order to damp an excess of energy due to an accidental increase of the power supply, transformed in an excessive temperature in heating means apt to transfer heat to said membrane, enabling the evaporation of the volatile substance.

This object is achieved, according to the present invention, by means of an electric evaporator for volatile substances, preferably a liquid formulation of an active substance, contained in a closed container comprising a semi-permeable membrane, i.e. a flat wall, for diffusing the volatile substance. The membrane is apt to allow passing through emanating vapours of the volatile substance but is not permeable to the liquid contained in the container.

The container with the volatile substance therein is apt to be permeated through the membrane, being the volatilization of the substance low enough to avoid evaporation at room temperature.

The electrical evaporator device proposed by the invention comprises heating means, which comprises in turn a heating plate, which defines two separated chambers, i.e. a first chamber and a second chamber. In addition the heating means comprises a heat generator, for example an electrical resistance or the like, supplied through a usual plug for connection to the electric supply. The heat generator is apt to heat the container and cause evaporation of the volatile substance, being located inside the first chamber, between the heating plate and the plug apt to connect the heating means to main, for example comprising two contact pins adapted to be inserted in a socket. The heating plate is apt to transfer heat to the membrane of the container, located inside the second chamber adjacent to the first chamber, and thus producing vapour emanation of the volatile substance.

Inside the second chamber is housed the container with the volatile substance to be evaporated, whose membrane is heated by the heating means located in the other continuous chamber, i.e. the first chamber.

The heat generator can be placed in any extreme or intermediate position within the first chamber, also designated as heating chamber, i.e. from close to the heating plate to close to the plug.

The first chamber is defined by the heating plate and a first cover, being the second chamber defined by said heating plate and a second cover. The coupling to each other of said first cover and second cover, joined by means of mechanical engagement, constitutes an external case of the device, apt to house and protect the elements comprised by the evaporator device as well as support and guide the connection plug which supplies power to the heating means having likewise means of engagement between the container and the external case.

According to the invention the first chamber, also named heating chamber, wherein the heating means are located, comprises intensity regulation means for regulate the intensity of the vapours emanation by means of regulation the consumption of the active substance. The aforementioned intensity regulation means comprises at least one regulation opening, or regulation window, located in the first cover and whose area may be adjusted by a shutter, apt to be hand controlled by the user, enabling the exit of a heated air flow and apt to regulate the temperature, i.e. heat quantity, in the heating plate and so in the first chamber, and thus regulating the consumption rate of the volatile substance what means to regulate the intensity of the vapours emanation of said volatile substance. Thus the regulation opening is apt to close and open, completely or partly, the heating chamber and modify the heat and temperature inside the heating chamber therein, enabling thus the regulation of the evaporation rate.

The intensity regulation means comprises a turnable pin linked to the shutter and apt to move it along any intermediate position located between a maximum position wherein the regulation opening is completely closed and an off position wherein the regulation opening is completely open.

When an user actuates the pin and places it in the off position, the device does not work by means of a contact between said pin and an internal switch apt to interrupts the power supply to the heat generator, being the regulation opening completely open. By the other hand, when the pin is placed in the maximum position, the device works, and the regulation opening is completely closed so the heat flow to the surrounding atmosphere is interrupted being maximum the heat quantity accumulated in the first chamber, inhibiting its refrigeration, being maximum the temperature in the heating plate and thus being maximum the evaporation of the volatile substance.

Therefore, by means of the regulation of the heat flow and the heat quantity accumulated in the first chamber, by the situation of the pin that controls the opening rate of the regulation opening, it is achieved the regulation of the evaporation intensity. Obviously when the pin is located in any intermediate position, the evaporation intensity rate will be a direct proportion of the open area of the regulation opening.

Contrary to the regulation means comprised in the state of the art, the intensity regulation means proposed by the invention does not regulate the air flow of the vapours emanated, by means of the regulation of an opening located between a container of the volatile substance and the surrounding atmosphere, what correspond to the second chamber in the device of the invention. However, the device according to the present invention comprises intensity regulation means, for the regulation of evaporation intensity of the volatile substance, apt to regulate the heat flow in a closed first chamber, i.e. heating chamber, formed by the heating plate and the first cover of the external case, being said heating plate apt to transmit the necessary heat quantity to the membrane of the substance container, which is located in an adjacent chamber, i.e. the second chamber.

By means of this device it is possible to have a regulation of the heat flow in the closed heating chamber, which produces a heat transfer regulation, i.e. more or less heat transfer, from the heating plate to the container of the volatile substance. When the heat flow is interrupted in said first chamber, the heating plate temperature increases till a maximum temperature, thus producing a high evaporation rate of the active substance.

The device can work both in manual or automatic mode. The automatic operating mode works indefinitely if the power supply is not interrupted. At any moment the user can activate the manual operating mode or stop the operation of the vaporizer device.

The container can be manufactured by known processes such as injection of plastic or thermoforming, which provides mechanical consistency and allows printing thereon of the information necessary for the user concerning how it should be removed for use.

Obviously, the container, which is preferably removable, comprises a closed body which contains the volatile substance and releases vapours into the surrounding atmosphere, which are emitted from the volatile substance which is fluid, preferably liquid, but can also be powder or semiliquid, or a paste or a gel.

Before use, an impermeable protection film, removable at the moment of first use, is attached to the semi-permeable wall, i.e. the membrane. The protection film can be, for example, peelably coupled to the membrane to prevent the volatile substance from exiting before first use.

The vapour drawing flow, which in the above described device is obtained using means for heating, can be obtained in other ways, for example using means for forced ventilation incorporated in the diffuser or external thereof.

The electrical connector means can comprise a contact pin adapted to be inserted in the cigarette lighter socket of an automobile, or two contact leads adapted to be connected to an electrical battery.

BRIEF DESCRIPTION OF THE DRAWINGS

Further characteristic features and advantages of the present invention will better emerge, however, more clearly from the following detailed description of a preferred but non-exclusive embodiment of the invention, illustrated purely by way of nonlimiting example in the accompanying figures of the drawings, in which.

DETAILED DESCRIPTION OF THE EMBODIMENTS

Figure 1:
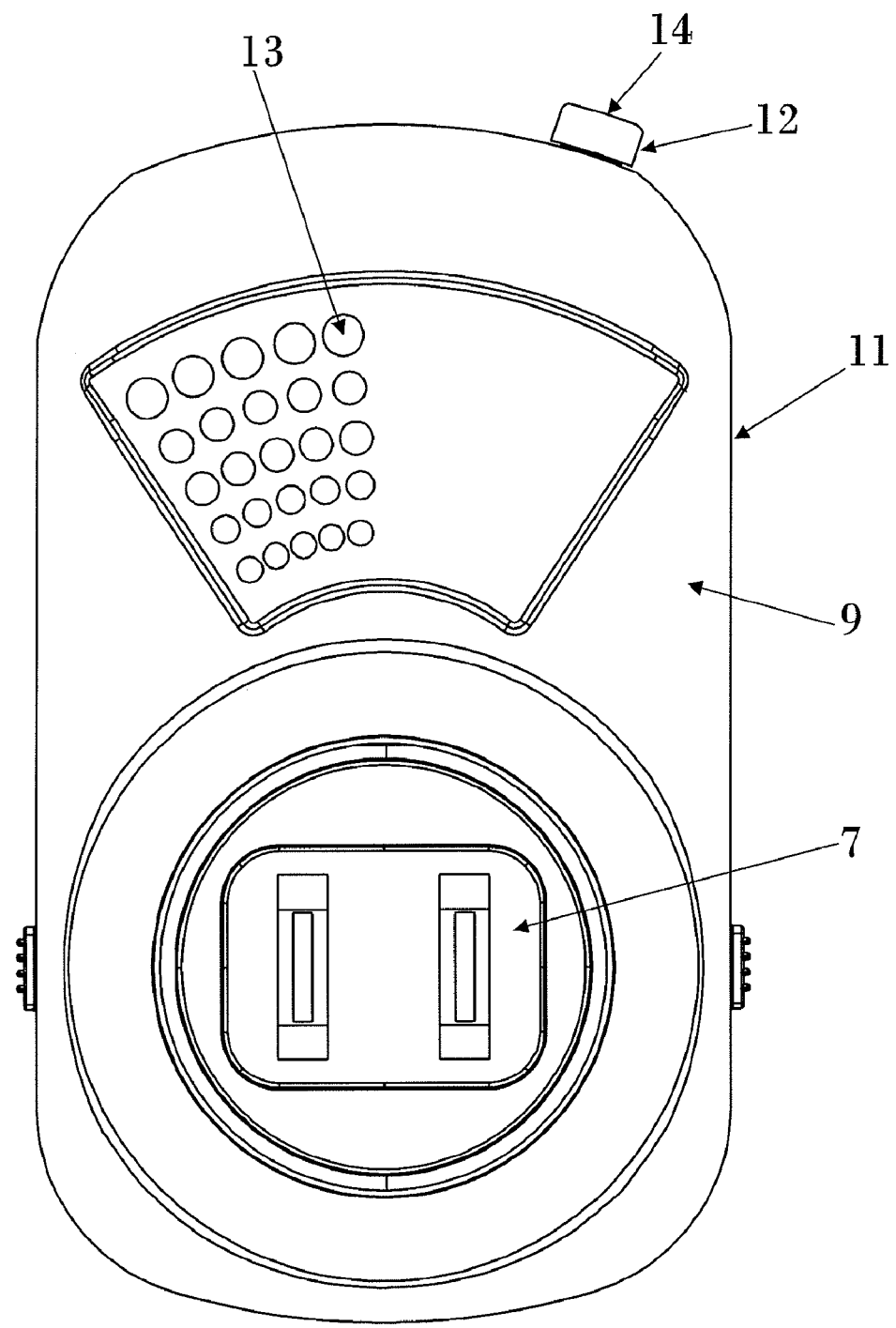
FIG. 1 shows a rear view of the electric evaporator device proposed by the invention.
Figure 2:
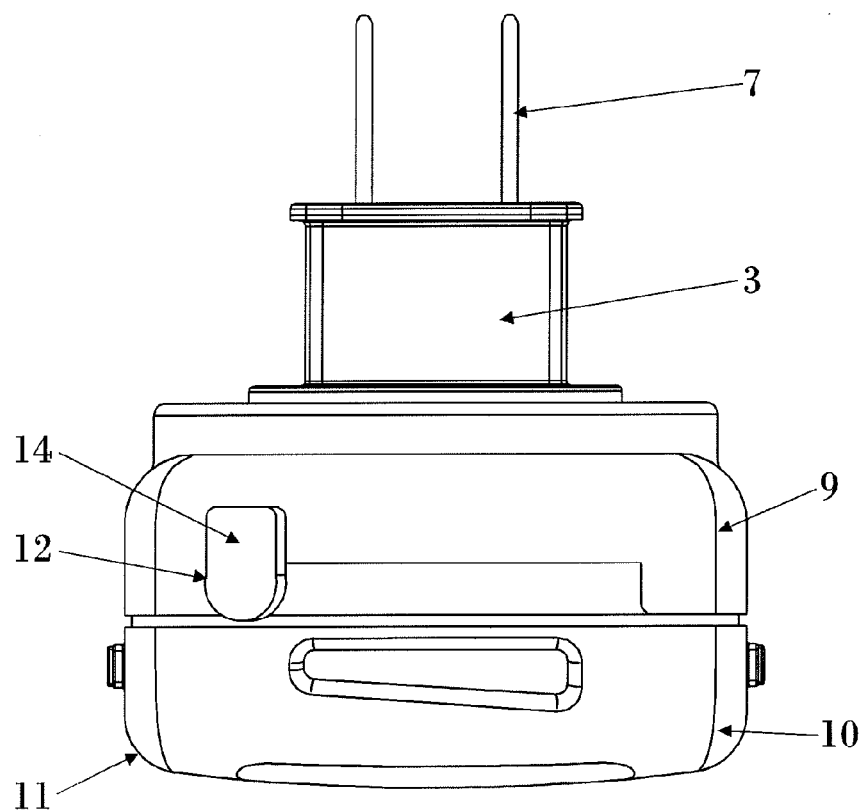
FIG. 2 shows a top view of the device, wherein the turnable pin is in the off position.
Figure 3:
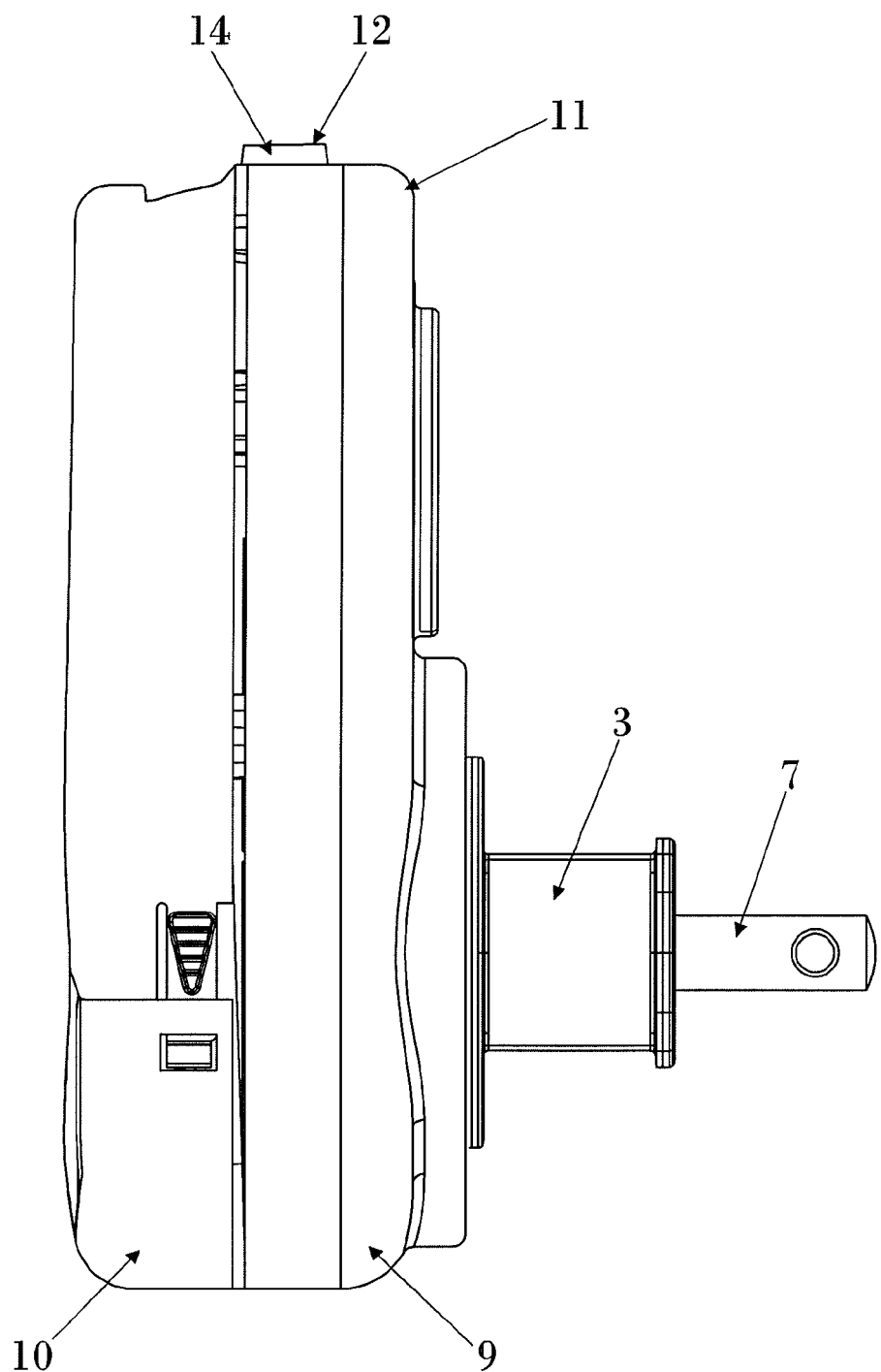
FIG. 3 shows a side view of the device.
Figure 4:
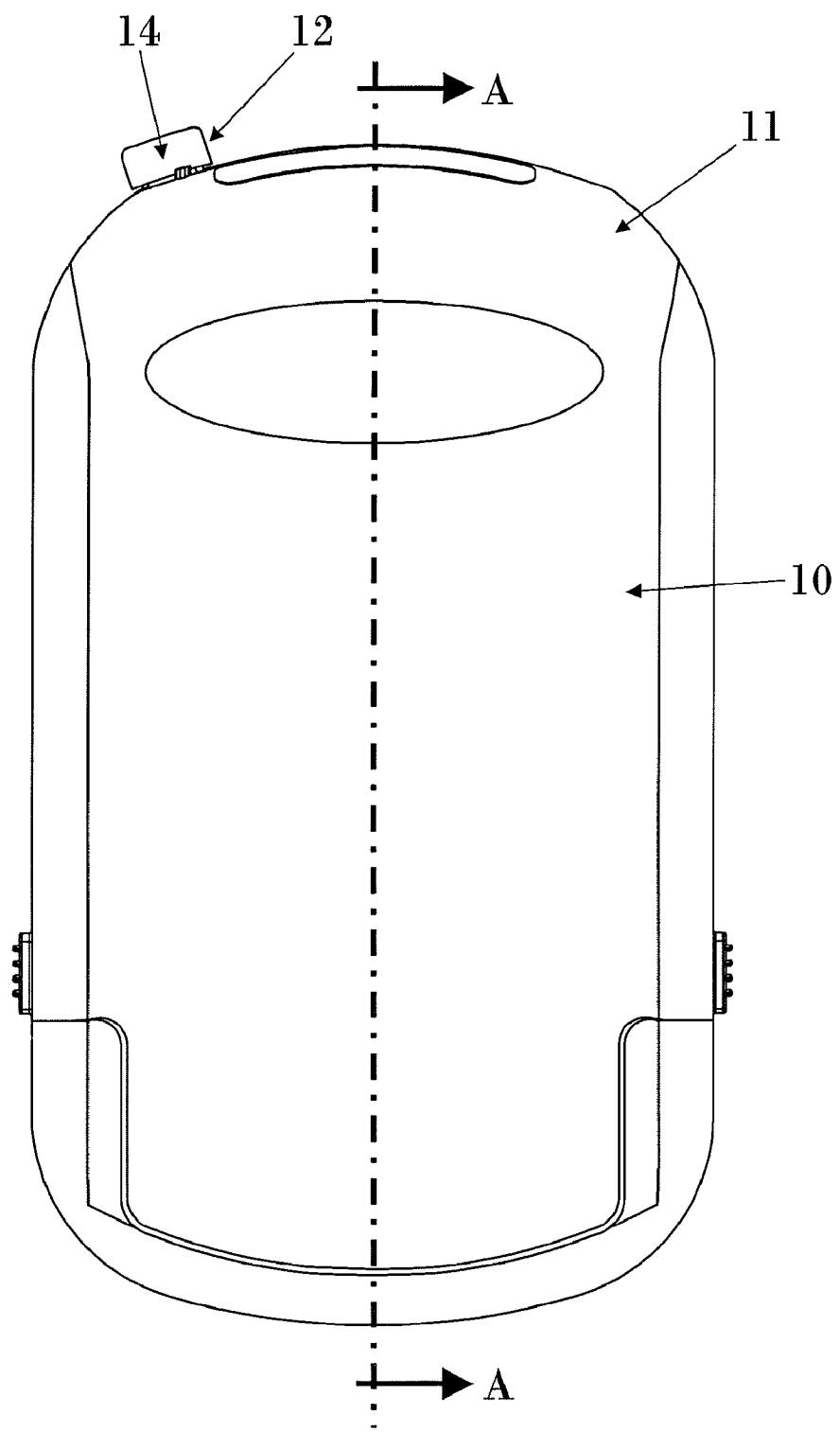
FIG. 4 shows a front view of the device.

As it can clearly be seen in the various views which are shown in the drawings, the evaporator according the present invention comprises a closed container (1) apt to contain volatile substances, preferably a liquid formulation of an active substance, comprising a semi-permeable membrane (2) apt to allow passing through emanating vapours of the volatile substance but not the liquid contained in the container (1), being the volatilization of the substance low enough to avoid evaporation at room temperature.

Furthermore, it is pointed out that the evaporator device comprises heating means (3), which comprises in turn a heating plate (4), which defines a first chamber (6) separated from a second chamber (8). The heating means (3) comprises a heat generator (5), consisting in an electrical resistance, supplied through a plug (7) for connection to the electric supply. The heat generator (5) is located inside the first chamber (6), between the heating plate (4) and the plug (7). The heating plate (4) is apt to transfer heat to the membrane (2) of the container (1) located inside the second chamber (8) adjacent to the first chamber (6).

Figure 8:
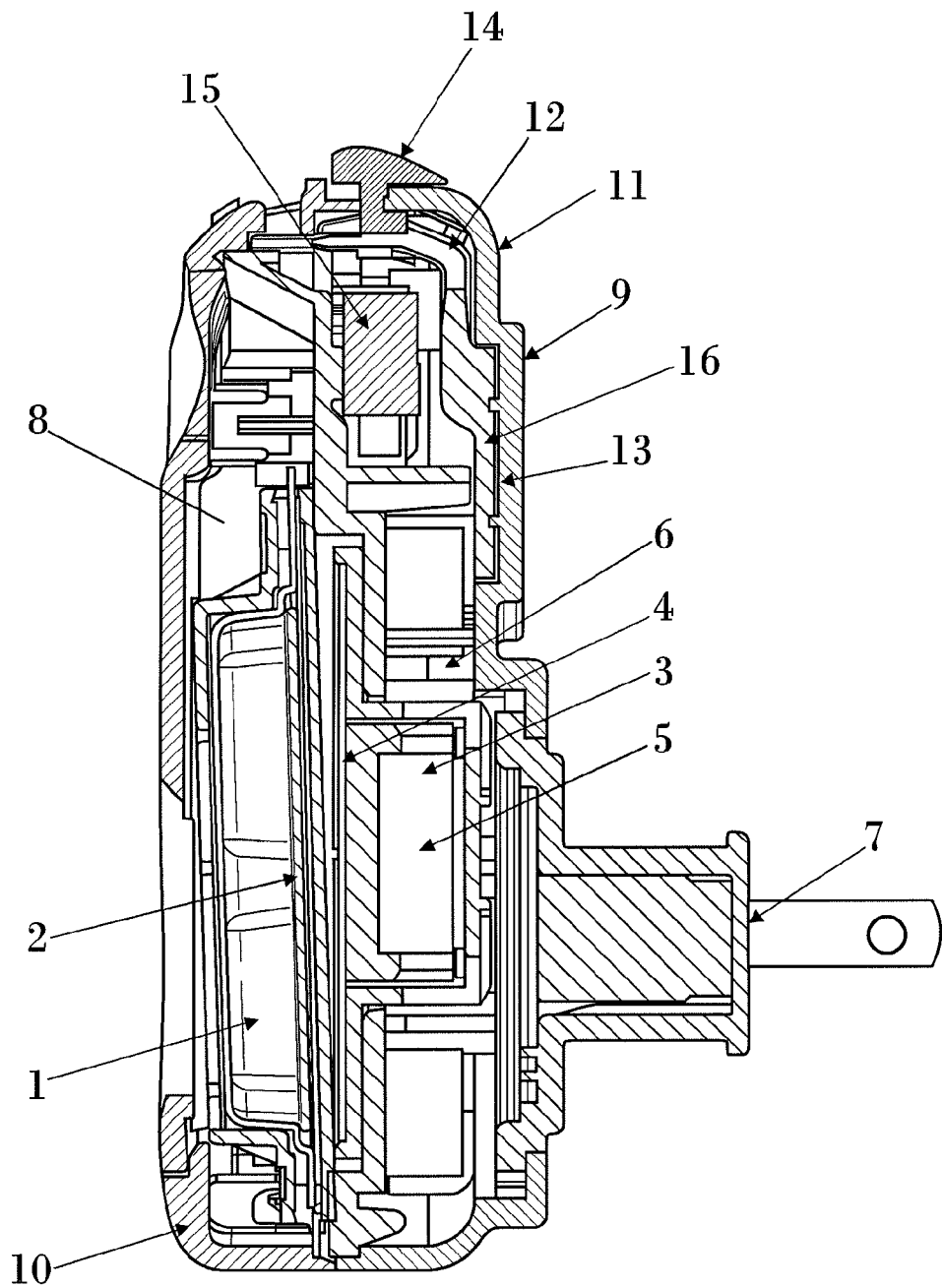
FIG. 8 show a side view in a cross-section of the device, wherein the heating plate, the container and the first and second chambers can be appreciated.

Such as is observed in FIG. 8, the first chamber (6) is defined by the heating plate (4) and a first cover (9), being the second chamber (8) defined by said heating plate (4) and a second cover (10). The first cover (9) and second cover (10) are coupled to each other by means of mechanical engagement, constituting an external case (11) of the device.

According to the invention the first chamber (6), with the heating means (3) therein, comprises intensity regulation means (12), for regulate the intensity of the vapours emanation, comprising a regulation opening (13) located in the first cover (9) and whose area may be adjusted by a shutter (16) linked with a turnable pin (14) apt to be hand controlled by the user, enabling the exit of a heated air flow and apt to regulate the temperature both in the first chamber (6) and the heating plate (4), enabling thus the regulation of the evaporation rate.

Figure 5:
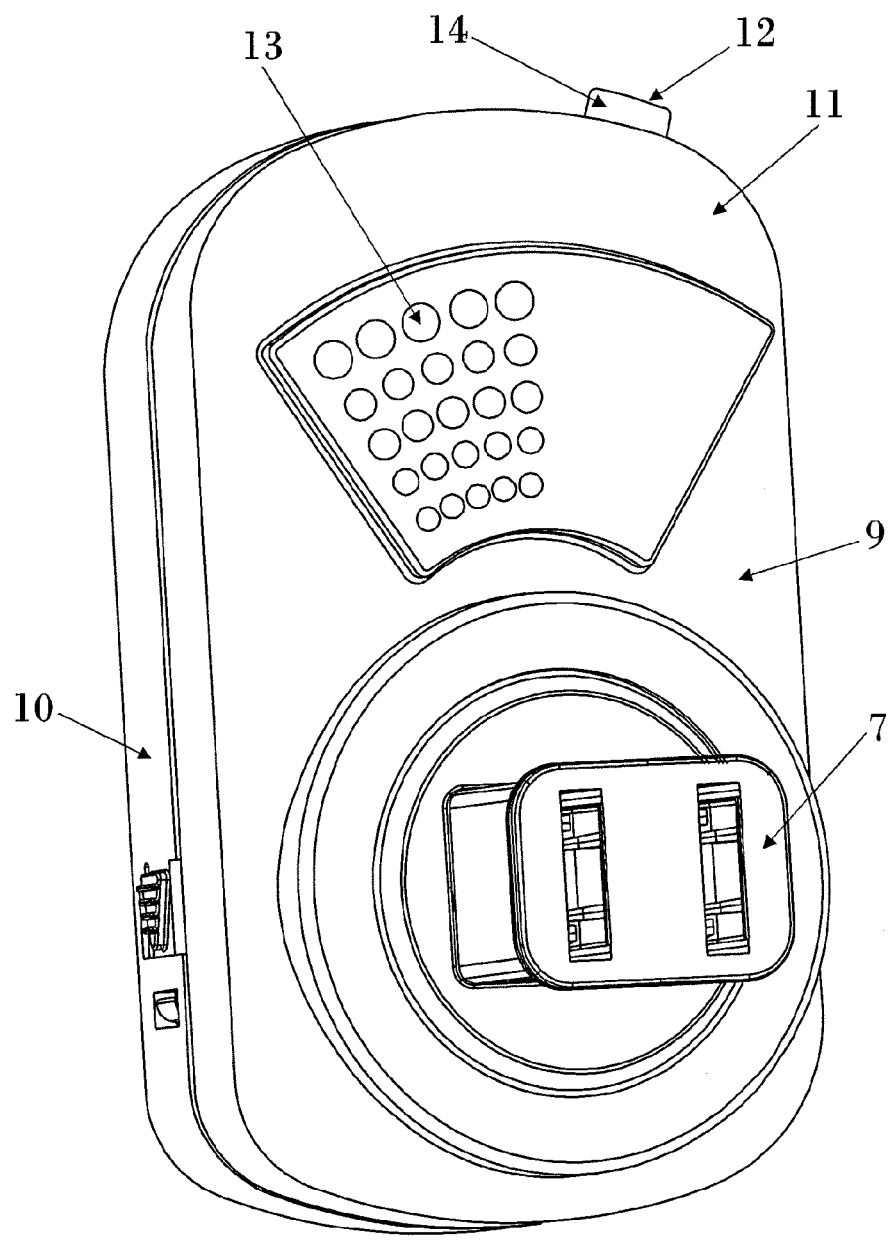
FIG. 5 shows a view in perspective of the device, wherein the regulation opening is in a complete open position, being the turnable pin in the off position as shown in FIG. 2.
Figure 6:
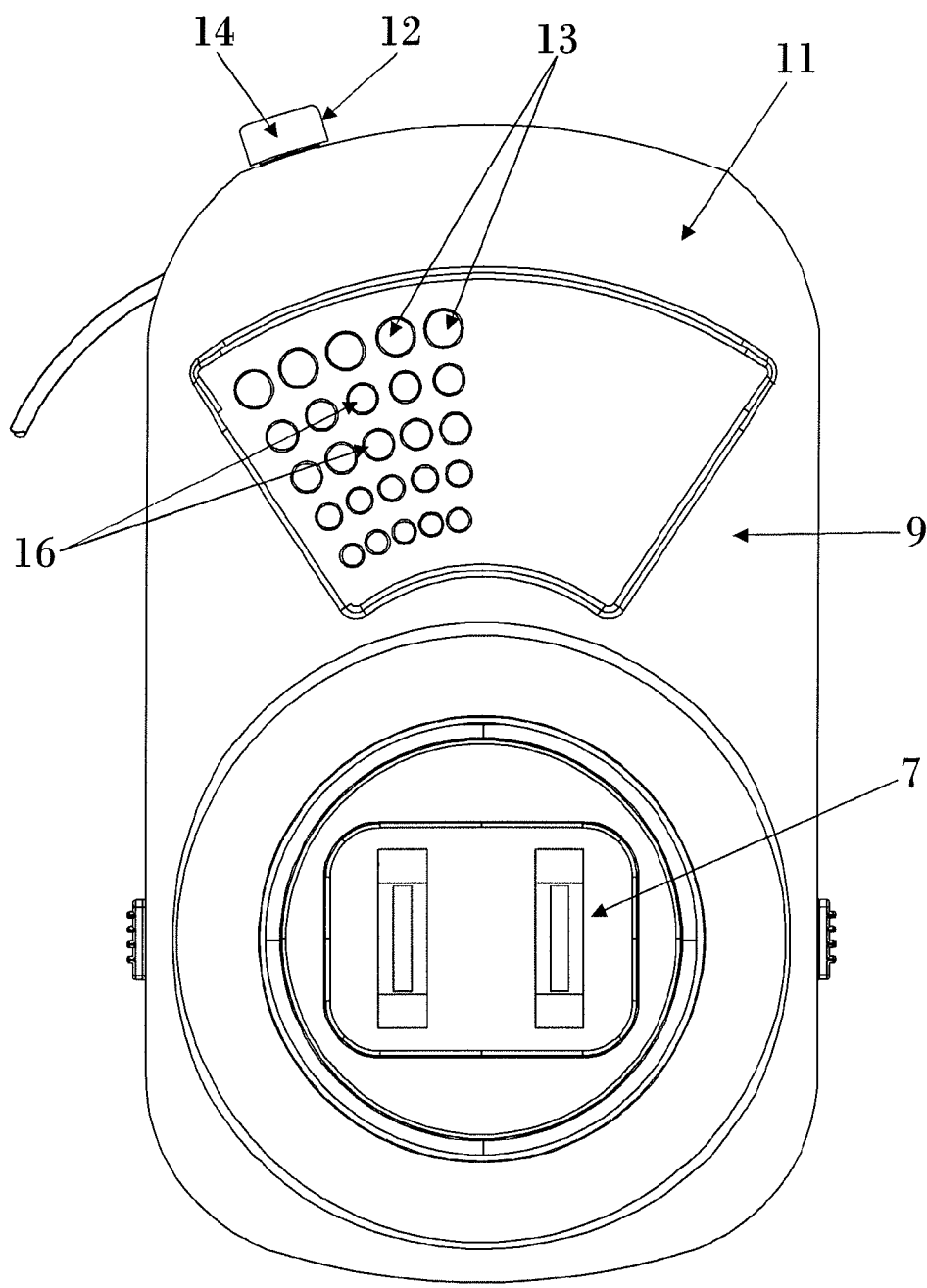
FIG. 6 shows a rear view of the device, wherein the regulation opening is in a complete closed position, being the turnable pin in the maximum position, contrary to shown in FIG. 5.
Figure 7A:
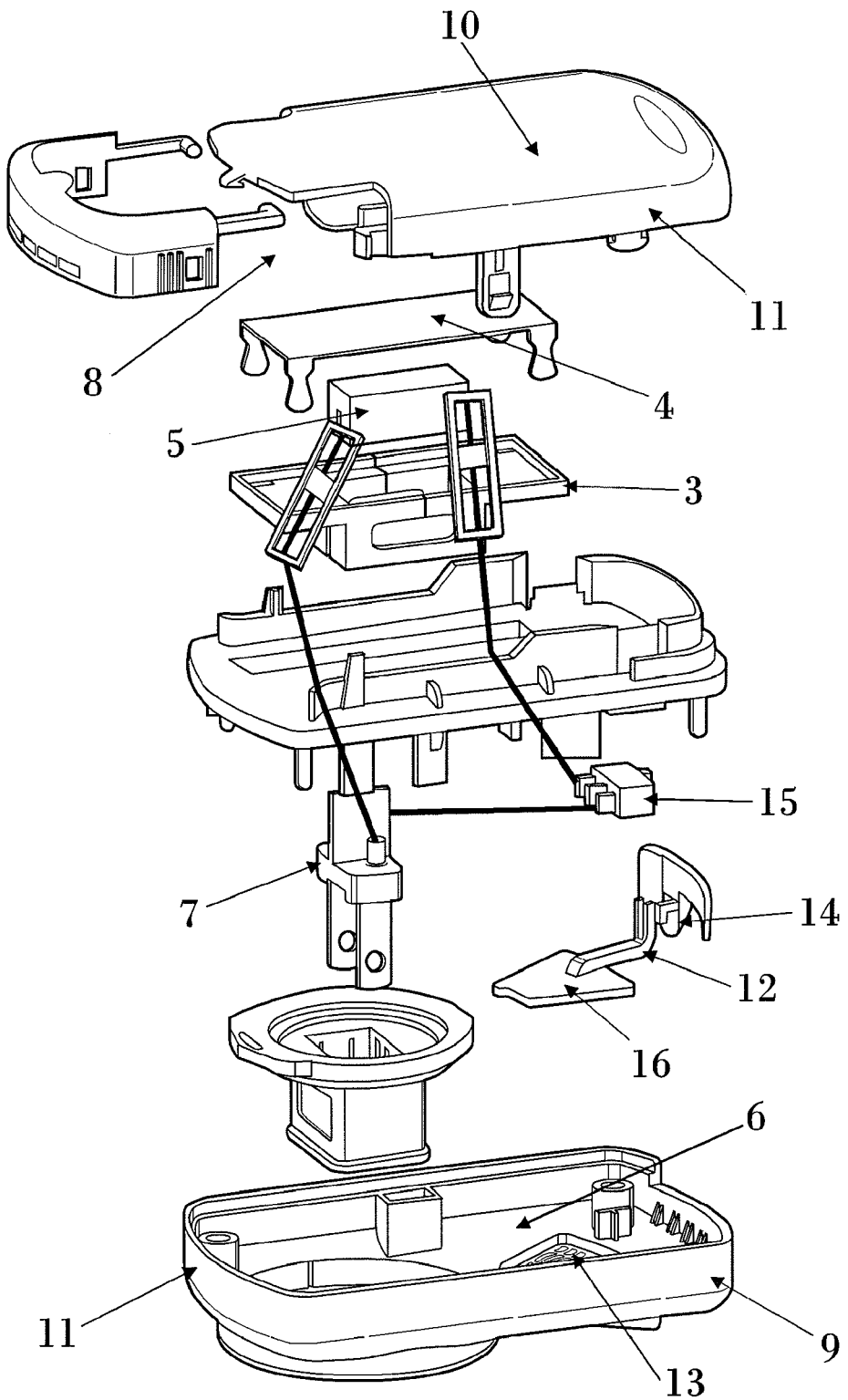
FIG. 7a and FIG. 7b show two exploded perspective views of the elements constituent the device.
Figure 7B:
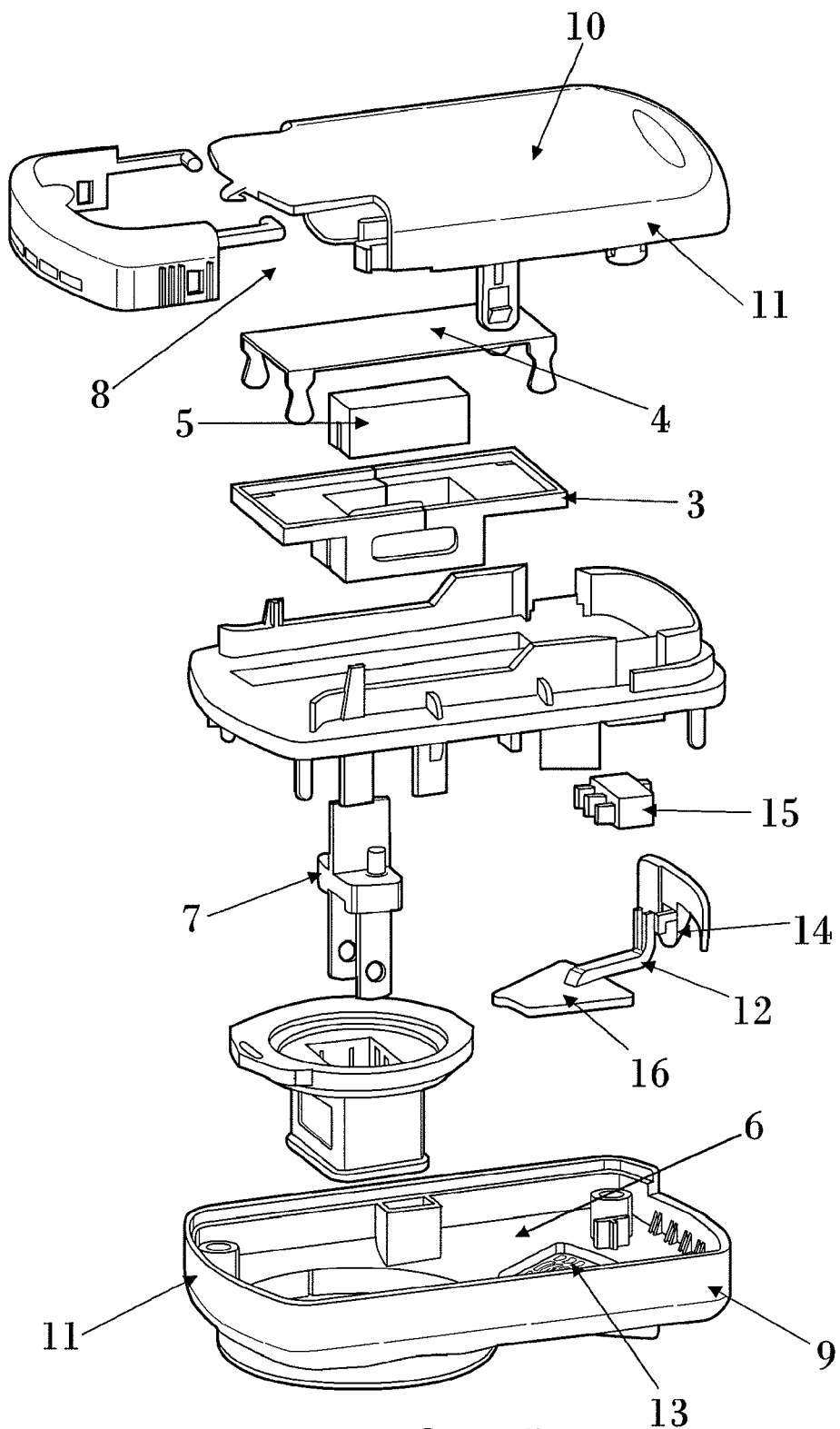

The pin (14) is apt move the shutter (16) along any intermediate position located between a maximum position wherein the regulation opening (13) is completely closed, as shown in FIG. 6, and an off position wherein the regulation opening (13) is completely open, as shown in FIG. 5.

When the pin (14) is placed in the off position, the device does not work by means of a contact between said pin (14) and an internal switch (15) apt to interrupts the power supply to the heat generator (5). Contrary, when the pin (14) is placed in the maximum position, the device works, and the regulation opening (13) is completely closed so the heat flow to the surrounding atmosphere is interrupted being maximum the heat quantity accumulated in the first chamber (6), and thus being maximum the evaporation of the volatile substance.

The pin (14) can be located in any intermediate position, being the evaporation intensity rate a direct proportion of the open area of the regulation opening (13).

The present invention has been described with reference to a preferred embodiment, but it is clear that the scope of protection of the invention is not limited thereto but is extended to include the numerous variations and modifications which are within the competence of a person skilled in the art who is acquainted with the present invention, provided that it falls within the scope of the accompanying claims.

What is claimed is:

1. Electric evaporator device of volatile substances with adjustable evaporation intensity, comprising:
    a container (1) apt to contain volatile substances comprising a semi-permeable membrane (2),
    heating means (3) comprising a heating plate (4), which defines a first chamber (6) separated from a second chamber (8), and a heat generator (5) located inside the first chamber (6),
    intensity regulation means (12) comprising at least a regulation opening (13), located in the first chamber (6), wherein the area of said at least one regulation opening (13) may be adjusted by a shutter (16), enabling the exit of a heated air flow and apt to regulate the temperature both in the first chamber (6) and the heating plate (4), enabling thus the regulation of the evaporation rate.

2. Device according to claim 1 wherein said container is arranged in said second chamber.

3. Device according to claim 1 wherein it further comprises a casing and said heating plate is arranged inside said casing, so that the first chamber is defined between one side of the heating plate and a part of said casing, and the second chamber is defined by the other side of the heating plate and an opposite part of the casing.

4. Device according to claim 1 wherein the heating plate is adapted for transmitting at least part of the heat in the first chamber to the second chamber.

* * * * *

UNITED STATES PATENT AND TRADEMARK OFFICE
CERTIFICATE OF CORRECTION

| | | |
|---|---|---|
| PATENT NO. | : 8,005,349 B2 | Page 1 of 1 |
| APPLICATION NO. | : 11/875502 | |
| DATED | : August 23, 2011 | |
| INVENTOR(S) | : Deflorian et al. | |

It is certified that error appears in the above-identified patent and that said Letters Patent is hereby corrected as shown below:

On the title page, Item [60] should read

[60]   Provisional application No. 60/862,339, filed on October 20, 2006.

Signed and Sealed this
Nineteenth Day of November, 2013

Teresa Stanek Rea
*Deputy Director of the United States Patent and Trademark Office*